United States Patent
Tolle et al.

(10) Patent No.: US 7,346,521 B2
(45) Date of Patent: Mar. 18, 2008

(54) SYSTEM AND METHODS FOR GENERATING PHYSICIAN PROFILES CONCERNING PRESCRIPTION THERAPY PRACTICES

(75) Inventors: Jill Tolle, Collegeville, PA (US); James Cain, Doylestown, PA (US)

(73) Assignee: IMS Health Incorporated, Plymouth Meeting, PA (US)

( * ) Notice: Subject to any disclaimer, the term of this patent is extended or adjusted under 35 U.S.C. 154(b) by 1141 days.

(21) Appl. No.: 09/941,496

(22) Filed: Aug. 29, 2001

(65) Prior Publication Data

US 2002/0165736 A1 Nov. 7, 2002

Related U.S. Application Data

(60) Provisional application No. 60/273,714, filed on Mar. 5, 2001.

(51) Int. Cl.
*A61B 5/00* (2006.01)
(52) U.S. Cl. .......................... 705/3; 128/897
(58) Field of Classification Search ............... 705/2–3; 128/897
See application file for complete search history.

(56) References Cited

U.S. PATENT DOCUMENTS

| | | | |
|---|---|---|---|
| 5,084,828 A | 1/1992 | Kaufman et al. ............ 364/479 |
| 5,737,539 A * | 4/1998 | Edelson et al. ................ 705/3 |
| 5,845,255 A | 12/1998 | Mayaud ........................... 705/3 |
| 6,014,631 A * | 1/2000 | Teagarden et al. .............. 705/3 |
| 6,305,377 B1 * | 10/2001 | Portwood et al. ........... 128/897 |
| 2002/0032582 A1 * | 3/2002 | Feeney et al. ................. 705/2 |

OTHER PUBLICATIONS

Written Opinion for PCT/US02/06268, dated Oct. 8, 2004.
International Search Report for PCT/US02/06268, dated Feb. 26, 2003.
Dendrite Corporation, Press Release "Dendrite Partners with Pharmacy Consortium to Deliver New Information to Better Direct Pharmaceutical Industry's Sales Forces", Sep. 14, 2000.
Dendrite Corporation, Press Release, "Dendrite Demonstrates How to Access To Its Critical Data Empowers Pharmaceutical Industry", Sep. 29, 2000.
Quintiles Transnational, Web pages "The Quinternet Services, Rx Market Monitor Selection", Jun. 20, 1999.

* cited by examiner

*Primary Examiner*—Florian Ryan Zeender
*Assistant Examiner*—Vanel Frenel
(74) *Attorney, Agent, or Firm*—Baker Botts LLP; Manu J. Tejwani (57) ABSTRACT

A system and methods for generating a profile concerning the prescription therapy practices of physicians in a therapeutic area of interest. A plurality of historical de-identified patient prescription records are analyzed, and the records are categorized based on changes in the dosage or the prescription product between prescriptions for a particular de-identified patient. The prescriptions may be categorized based on the duration between the due date of a prescription and the date the prescription was filled. This information may be summarized for each physician for each product in the therapy area of interest.

35 Claims, 10 Drawing Sheets

| | PRODUCT | DOSAGE | START |
|---|---|---|---|
| 1 | DRUG #1 | 20MG | FRI 2/12/99 |
| 2 | DRUG #1 | 20MG | TUE 3/9/99 |
| 3 | DRUG #1 | 40MG | THU 3/25/99 |
| 4 | DRUG #2 | 150MG | FRI 4/23/99 |
| 5 | DRUG #2 | 225MG | FRI 5/7/99 |
| 6 | DRUG #2 | 225MG | SAT 5/22/99 |
| 7 | DRUG #2 | 225MG | SAT 6/5/99 |
| 8 | DRUG #2 | 300MG | TUE 6/22/99 |
| 9 | DRUG #3 | 75MG | FRI 7/2/99 |
| 10A | DRUG #2 | 75MG | THU 7/8/99 |
| 10B | DRUG #2 | 300MG | THU 7/8/99 |
| 10C | DRUG #4 | 15MG | THU 7/8/99 |
| 11A | DRUG #2 | 75MG | THU 7/22/99 |
| 11B | DRUG #2 | 300MG | THU 7/22/99 |
| 11C | DRUG #4 | 15MG | THU 7/22/99 |
| 12 | DRUG #4 | 30MG | WED 7/28/99 |
| 13a | DRUG #2 | 300MG | SAT 8/7/99 |
| 13b | DRUG #2 | 75MG | SAT 8/7/99 |
| 14 | DRUG #4 | 30MG | TUE 8/17/99 |
| 15 | DRUG #2 | 300MG | SAT 8/21/99 |
| 16 | DRUG #2 | 75MG | SAT 8/21/99 |

352 — PHYSICIAN
DOE. JOHN

354 — PRODUCT
DRUG #1

356 — 20  NEW THERAPY START(S)
358 — 27  CONTINUED THERAPY
360 — 10  THERAPY SWITCH
362 — 5   TITRATION INCREASE
364 — 8   TITRATION DECREASE
366 — 80% PERSISTENCE
368 — 75% COMPLIANCE

EARLYVIEW - EARLYVIEW REPORT (JUL 1999 - JUL 2000)
TOP 50 PRESCRIBERS FOR ROLLING 12M MARKET VOL
KEY PRODUCTS: DRUG #1, DRUG#2

EARLYVIEW SUMMARY

| MARKET SALES FORCE TERRITORY | :CHRONIC PAIN :275 :04001099 | | | | | | | | | | | | | | |
|---|---|---|---|---|---|---|---|---|---|---|---|---|---|---|---|
| PRODUCT | LRx TREND | R12M NRX VOL | JUN'00 06/30 | JUL'00 07/07 | JUL'00 07/14 | JUL'00 07/21 | JUL'00 07/28 | AUG'00 08/04 | AUG'00 08/11 | AUG'00 08/18 | AUG'00 08/25 | SEP'00 09/01 | SEP'00 09/08 | SEP'00 09/15 | SEP'00 09/22 |
| | | | | | | | NRx MARKET SHARE (%) | | | | | | | | |
| DRUG #1 | N | 1196 | 21.3 | 23 | 17.9 | 23.6 | 25.7 | 21 | 22 | 16.5 | 17.2 | 13.9 | 15.8 | 16.7 | 17.6 |
| DRUG #2 | U | 4594 | 67.5 | 62.6 | 70.1 | 64.2 | 64.3 | 70.1 | 69.8 | 76.2 | 74.6 | 78.7 | 76.2 | 76.4 | 76.1 |
| MKT VOL | | 6345 | 372 | 367 | 415 | 415 | 443 | 507 | 504 | 496 | 623 | 531 | 658 | 677 | 672 |

| MARKET SALES FORCE TERRITORY | :CHRONIC PAIN :275 :04001099 | | | | | | | | | | | | | | |
|---|---|---|---|---|---|---|---|---|---|---|---|---|---|---|---|
| PRESCRIBER | LRx TREND | R12M NRX VOL | JUN'00 06/30 | JUL'00 07/07 | JUL'00 07/14 | JUL'00 07/21 | JUL'00 07/28 | AUG'00 08/04 | AUG'00 08/11 | AUG'00 08/18 | AUG'00 08/25 | SEP'00 09/01 | SEP'00 09/08 | SEP'00 09/15 | SEP'00 09/22 |
| | | | | | | | NRx MARKET SHARE (%) | | | | | | | | |
| DOE, JOHN 5240583058 (21) 34 DENNY DRIVE CALYPSO MA 02150 | | | | | | | | | | | | | | | |
| DRUG #1 | D | 38 | 10.1 | 9.7 | 22.2 | 17.5 | 19.8 | 15.4 | 17.7 | 18.3 | 16.4 | 8.3 | 17 | 18.2 | 26.9 |
| DRUG #2 | U | 164 | 71.4 | 73.2 | 70.4 | 82.5 | 75 | 84.6 | 72.1 | 81.7 | 76.6 | 84.3 | 83 | 76 | 68.4 |
| MKT VOL | | 213 | 14 | 15 | 17 | 7 | 20 | 25 | 21 | 20 | 15 | 15 | 14 | 19 | 24 |
| THIS PRESCRIBER IS SHOWING RAPID SWITCHING BEHAVIOR FROM DRUG #1 TO DRUG #2 SINCE DECEMBER. | | | | | | | | | | | | | | | |
| SMITH, MARY 0240583012 (4) 151 EVERETT AVE CHELSEA MA 02150 INTERNAL MEDICINE | | | | | | | | | | | | | | | |
| DRUG #1 | N | 38 | 10.1 | 9.7 | 22.2 | 17.5 | 19.8 | 15.4 | 17.7 | 18.3 | 16.4 | 8.3 | 17 | 18.2 | 26.9 |
| DRUG #2 | N | 164 | 71.4 | 73.2 | 70.4 | 82.5 | 75 | 84.6 | 72.1 | 81.7 | 76.6 | 84.3 | 83 | 76 | 68.4 |
| MKT VOL | | 213 | 14 | 15 | 17 | 7 | 20 | 25 | 21 | 20 | 15 | 15 | 14 | 19 | 24 |
| SLOWLY MAKING DRUG #2 THE CHOICE OF SECONDARY THERAPY, REPLACING DRUG #1, TREND STARTING JUNE OF 2000 | | | | | | | | | | | | | | | |
| ADAMS, JOHN 4954565009 (1) 3 WOODLAND RD, SUI STONEHAM MA 02180 | | | | | | | | | | | | | | | |
| DRUG #1 | U | 63 | 5 | 6 | 2.4 | 6.2 | 13.8 | 6.8 | 5 | 2.3 | 5.6 | 6.4 | 5.9 | 2.9 | 7.9 |
| DRUG #2 | U | 917 | 85.9 | 77.9 | 83 | 78.9 | 72.4 | 88 | 86.5 | 87.2 | 86.9 | 83.9 | 80.2 | 89.8 | 85.2 |
| MKT VOL | | 1093 | 63 | 48 | 71 | 75 | 57 | 67 | 56 | 68 | 114 | 124 | 148 | 133 | 131 |
| NEW THERAPY STARTS SIGNIFICANTLY ABOVE AVERAGE MARKET SHARE; STEADY DECLINE IN THE USE OF DRUG #1 FOR NEW THERAPY STARTS SINCE SEPTEMBER | | | | | | | | | | | | | | | |
| MARTIN, MIKE 0432852025 (123) 2 RANCH AVENUE SUDBURY MA 01776 | | | | | | | | | | | | | | | |
| DRUG #1 | N | 91 | 37 | 28.4 | 33 | 31 | 30.7 | 59.2 | 60.3 | 64.4 | 72.5 | 51.1 | 58.6 | 48 | 47.4 |
| DRUG #2 | N | 73 | 53.7 | 50 | 49.9 | 61.2 | 54.1 | 24.4 | 33.8 | 28.5 | 19.3 | 38.4 | 34 | 45.1 | 44.4 |
| MKT VOL | | 185 | 13 | 18 | 15 | 16 | 8 | 15 | 21 | 17 | 15 | 12 | 16 | 18 | 15 |
| TITRATING UP ON DRUG #1 SLOWER THAN AVERAGE; DEMONSTRATING SWITCHING BEHAVIOR TO OTHER THERAPIES / DRUGS FASTER THAN OTHER PRESCRIBERS/PRESCRIPTIONS | | | | | | | | | | | | | | | |

SYSTEM AND METHODS FOR GENERATING PHYSICIAN PROFILES CONCERNING PRESCRIPTION THERAPY PRACTICES

CROSS-REFERENCE TO RELATED APPLICATION

This application claims priority on U.S. Provisional Patent Application Ser. No. 60/273,714, entitled "Physician Profiling for Enhanced Sales Force Targeting Using Longitudinal Rx Data (LRx)," which was filed on Mar. 5, 2001, and which is incorporated by reference in its entirety herein.

BACKGROUND OF THE INVENTION

1. Field of the Invention

The invention relates to systems and methods for analyzing prescription claim histories for physicians, and determining statistics about the prescription therapies of such physicians.

2. Related Art

Pharmaceutical sales representatives typically determine a territory call plan based on information about physicians in their respective coverage areas, and the range of pharmaceutical products that such physicians typically prescribe. This information may include the specialty of the physician, the physician's response to promotional efforts, the physician's ranking in the pharmaceutical product's market share, the physician's ranking in total market volume, and the physician's ranking in the pharmaceutical product's prescription volume. Based on observed patterns with respect to this information, further qualities about physicians have been successfully modeled such as "new product early adopter," which refers to physician who tends to prescribe a new product soon after it becomes available, or "brand loyalist," which refers to a physician who continues to prescribe a specific branded drug, even in the face of competitive drug availability.

While the above information is derived from prescriptions written by the physicians, the information does not provide insight into either physicians treatment practices over a given period of time, or such practices as applied to different patient types. Such targeting would require a more detailed understanding of a physician's treatment practices within his patient population, e.g., through the formation of a database of prescription activity for each physician where de-identified patients can be tracked to understand how a physician prescribes in a particular therapeutic area.

Although algorithms have been developed for use on longitudinal medical records, these applications have been for market research or summarized levels of analysis. Outcome research and market research on longitudinal prescription data is currently being offered through several vendors—all utilizing single sources of data for their applications.

Accordingly, there exists a need in the art for a technique which can analyze the long term prescribing practices of physicians, including the ability to provide information about changes in both dosages and products prescribed by the physicians and the ability to provide information about the tendencies of a physician's patient population to follow prescribed regimens.

SUMMARY OF THE INVENTION

An object of the present invention is to provide a technique for analyzing the prescription practices of multiple physicians over a given period of time.

Another object of the present invention is to provide prescription activity analysis tools which can assist pharmaceutical sales representatives in understanding the prescription practices of physicians.

A further object of the present invention is to provide a technique which can track changes in prescription dosages prescribed by a physician.

A still further object of the present invention is to provide a technique for monitoring patient population tendencies to follow prescriptions regimens.

These and other objects of the invention, which will become apparent with reference to the disclosure herein, are accomplished by a system and method for generating a longitudinal physician profile concerning the prescription therapies for de-identified patients issued by one or more physicians in a particular therapeutic area of interest. A physician profile may be generated on a computer system including a mass storage device containing de-identified historical patient prescription records categorized by de-identified patient, physician, prescription product and dosage.

The historical de-identified patient prescription records may be retrieved from the mass storage device by a dynamic memory, and user-specified information may be provided to define a subset of the historical de-identified patient prescription records. Particular historical prescription data within the subset of data defined by the user-specified information may be extracted to provide a set of data including de-identified patients that meet certain eligibility requirements.

In one preferred arrangement, the categorization process of each prescription may include comparing the dosage and prescription product for a particular prescription for each patient with the dosage and prescription product of another prescription for the patient. The categorization of the particular prescription is based on a change in the dosage or in the prescription product between the particular prescription and the other prescription. Particular categories of prescriptions may include a new therapy start, a therapy switch, an add-on therapy, a titration increase or decrease, or a continued therapy.

Advantageously, persistence may be determined both for each particular patient, as well as for all patients for each physician. The patient prescription data may be extracted with a second subset of data defined by a categorizing step. For example, prescriptions that are a therapy switch or a titration may be excluded from the compliance/persistence analysis. The duration between a due date of a particular prescription and the date the prescription was filled may be determined. The particular prescription may be categorized based on the duration between the due date and the date the prescription was filled.

In accordance with the invention, the objects as described above have been met, and the need in the art for a technique which can analyze the long term prescription practices of a group of physicians, including the ability to provide information about changes in both dosages and products prescribed by the physicians and the ability to provide information about the tendencies of a physician's patient population to follow prescribed regimens, has been satisfied. Further features of the invention, its nature and various

BRIEF DESCRIPTION OF THE DRAWINGS

FIG. 10 is an exemplary summary report in accordance with the invention.

DETAILED DESCRIPTION OF THE PREFERRED EMBODIMENTS

Figure 1:
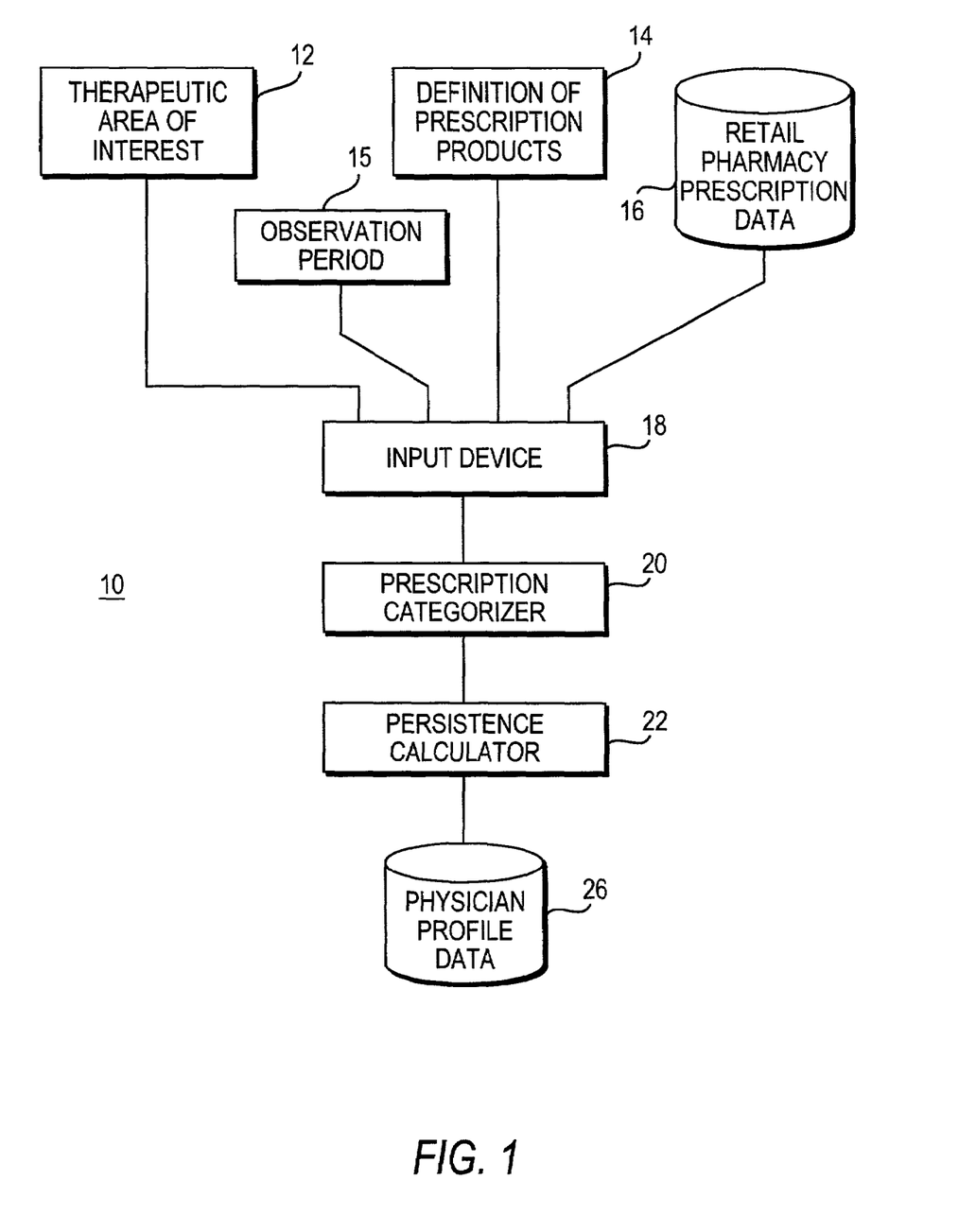
FIG. 1 is a block diagram of an exemplary system in accordance with the invention.

Referring now to FIG. 1, an illustrative embodiment of a system for processing prescription data is depicted and generally referred to as system 10. The system 10 may utilize several sources of information for processing. The user supplies information on a particular therapeutic area or market of interest 12, such as an anti-depressant therapy or blood pressure control therapy. The user may also supply information on certain prescription products which are to be included in the study 14. Time period information 15, i.e., an "observation period," is selected by the user to specify the period of time in which to monitor the dispensing of prescriptions. Information on the specific prescriptions is included in prescription data, i.e., Retail Pharmacy Prescription data 16, which includes historical de-identified patient prescription data and is typically stored on a mass storage device. This input information in received by the system at the input device 18.

The physician targeting system 10 uses longitudinal prescription data from retail pharmacies. Retail Pharmacy Prescription data 16 supplies information such as the prescription product dispensed, the dosage, refill information, i.e., an indication of whether or not a refill is authorized, the day supply, i.e., the number of days until the patient will need a refill, and the date dispensed. Retail Pharmacy Prescription data 16 groups the above information for one patient under a "de-identified" patient identification number. The de-identified patient identification number is an identifier that replaces a patient's name and protects patient confidentiality since it provides no personal information about the patient. This information allows the system to track prescription therapy over time for one specific, although unknown, patient. Thus whenever a "patient" or "patient data" is described herein, it is understood that the patient's identity and personal information are excluded (i.e., the patient is "de-identified") in order to maintain confidentiality of patient records.

While the disclosure herein is described with use of Retail Pharmacy Prescription data, other data structures could readily be employed, such as Pharmacy Benefit Manager (PBM) prescription claims data, mail order prescription data, or a combination of data sources.

A prescription categorizer 20 and compliance and persistence calculator 22 perform a series of data processing operations by the central processing unit of a computer, executing software programs in COBOL, which are stored in dynamic computer memory, such as RAM (not shown). The input data is received by the prescription categorizer 20 which first considers whether each de-identified patient is "track-able" to be included into the prescription categorization process. Once track-ability is confirmed, then the prescription categorizer 20 compares the dosage and prescription product for a particular prescription for a each de-identified patient with the dosage and prescription product of another prescription for that de-identified patient identification number and categorizes the particular prescription based on a change in the dosage or the prescribed medication between the particular prescription and the other prescription. Each prescription may be categorized by the prescription categorizer 20 into the following categories: (1) New Therapy Start, (2) Therapy Switch, (3) Add-on Therapy (concomitant), (4) Titration Decrease, (5) Titration Increase, or (6) Continued Therapy. Those skilled in the art will understand that other categories could be added.

The persistence calculator 22 compares the due date of a particular prescription for a de-identified patient with the date the subsequent prescription was actually filled. The persistence calculator 22 also categorizes the de-identified patient based on the number of days between the due date and the date the prescription was filled. The above calculations performed by the software program. Persistence in the prescription data refers to a de-identified patient's diligence in following their physician's prescription therapy. The persistence calculator may also summarize the categories of de-identified patients for each physician. Compliance is a measure attributed to the physician derived from the percentage of days that persistent de-identified patients were on a prescription therapy when compared with the number of days that the de-identified patients were supposed to be on that therapy. These two measures are determined by the compliance and persistence calculator 22. This information is organized into a summary which is stored as output data 26. This is described in greater detail as noted below with respect to FIGS. 9-10.

The procedures implemented by the present invention are described with respect to FIGS. 2-3 and 5-8. The foregoing procedures may be implemented on a general purpose computer (not shown) including a suitable input device 18 and mass storage 26. With specific reference to FIG. 2, information on the therapeutic area of interest, the prescription products included in the study, and the observation period is received at step 100. The Retail Pharmacy Prescription data for the transactions to be included in the study are received at step 102. Note that these steps may proceed consecutively or concurrently. Subsequently, each of the prescriptions are categorized into one of several predetermined categories, as listed above, in step 104. Compliance and persistence information is determined at step 106. A summary of information determined in steps 104 and 106 is generated and stored at step 108.

Figure 3:
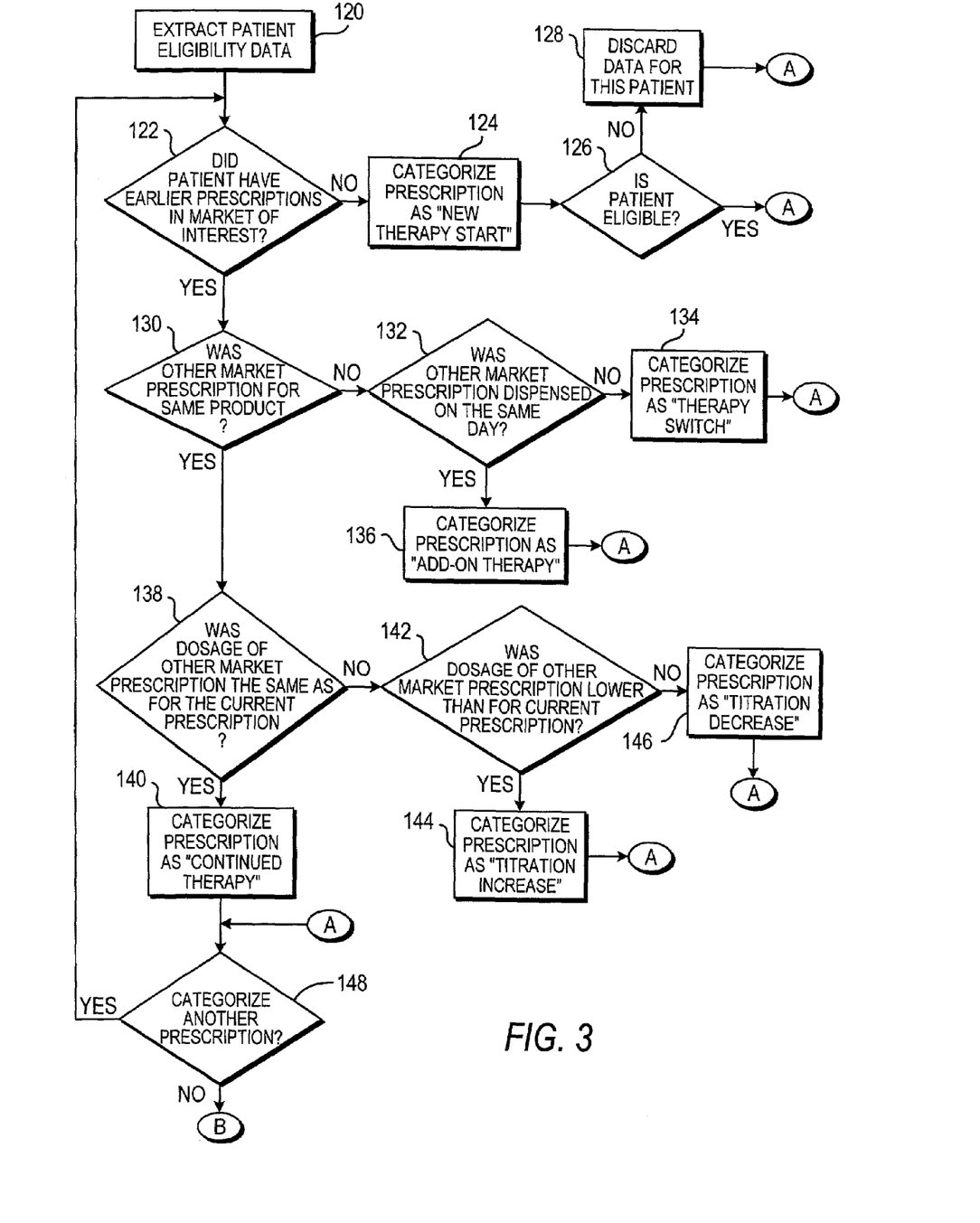
FIG. 3 is a flowchart illustrating a portion of the procedure of FIG. 2 in greater detail in accordance with the invention.

Further details of step 104 are illustrated in FIG. 3. In order for a de-identified patient's prescription to be included into the longitudinal prescription categorization process, patient eligibility files are used to determine if a de-identified patient has been prescription benefit eligible for a specified number of weeks, i.e., the observation period. This minimum period of time is useful to get a full view of a de-identified patient's prescription therapy history. For example, a de-identified patient who is newly enrolled in a health plan would not have sufficient historical information to determine whether a prescription was a continuation or a change in a particular therapy. Thus, if the de-identified patient is not considered eligible, the data for that de-identified patient is discarded.

Information on the therapeutic area, the prescription products of interest, and observation period received in step 100 and Retail Pharmacy Prescription data received in step 102 are passed on to step 120 where a patient eligibility extract is generated. A filter is used to create a list of de-identified patient identification numbers for patients that are eligible for the prescription plan during the observation period. The patient eligibility extract may also be limited to the specified products in the specified market of interest as defined by the user.

Steps 122-146 may be performed for each prescription in the analysis. The prescription being categorized in steps 122-146 is referred to herein as the "current prescription." The process of categorization for the current prescription begins at step 122. In accordance with a preferred embodiment of the invention, it is determined whether the current prescription is a "New Therapy Start" for the de-identified patient at step 122. A New Therapy Start may be defined as the first prescription that a de-identified patient receives in the market of interest. This is performed by searching the records to see if the de-identified patient has any earlier prescriptions in the market of interest during the observation period. If there were no other prescriptions in this market for that de-identified patient and the current prescription has a "new prescription" indicator in the Retail Pharmacy Prescription data, then the current prescription is categorized as a New Therapy Start (step 124).

At step 126, a prescription that has been categorized as "New Therapy Start" is compared to the patient eligibility extract. If the de-identified patient identification number on the current prescription is not listed in the patient eligibility extract, then the current prescription is discarded from the categorization process for this de-identified patient at step 128. The process continues with the next prescription as indicated by marker A in FIG. 3

If there was at least one other "market prescription," defined as a previous prescription in the market of interest during the observation period, then the analysis proceeds to step 130. This step determines whether that other market prescription was for the same product as the current prescription. If the other market prescription was for a different product, the analysis proceeds to step 132. There are two preferable categories when the other market prescription was for a different product: (1) a "Therapy Switch" which occurs when a de-identified patient receives a prescription for a different product than the last one they received, and (2) an "Add-on Therapy" occurs when a de-identified patient appears to be taking more than one product at a time, i.e., the prescription is "added-on" to other market prescriptions, as will be described in greater detail herein.

At step 132, the dates of the current prescription and the other market prescription are considered. If the other market prescription was not dispensed on the same day as the current prescription, then the current prescription is categorized as a Therapy Switch at step 134 and the process is finished for the current prescription. The current prescription may also store information on the product it was switched from. However, if the current prescription and the other market prescription were dispensed on the same date, then the current prescription is considered to be an Add-On Therapy at step 136, and the process is finished for the current prescription. After steps 134 and 136, the process continues with the next prescription as indicated by marker A. Although the embodiment described herein defines a prescription having the same date as an Add-On therapy, the system may be configured to permit a date range or window that would further define the difference between a therapy switch and an add-on.

If the step 130 determined that the current prescription and the other market prescription are for the same product, then analysis proceeds to step 138. There are three preferable categories for a current prescription which is for the same product as the other market prescription in the records: (1) A Continued therapy is a prescription at the same dosage level as the de-identified patient's last prescription; (2) A Titration Increase is a prescription for the same product at a greater dosage level than that de-identified patient's last prescription; and (3) A Titration Decrease is a prescription for the same product at a smaller dosage level. Other categories of prescriptions could also be utilized.

At step 138, the daily dosages for the current prescription and the other market prescription are compared. Dosage is computed as the strength of the product multiplied by the amount of product to be taken each day. For example, product Y may have a strength of 50 mg and require 2 pills per day. The daily dosage for product Y is therefore 100 mg (i.e., 50 mg * 2 pills). Other measures of dosage rate may be utilized as appropriate. If the dosages for the current prescription and the other market prescription are the same, or if either of the dosages is invalid then the current prescription is categorized as a Continued Therapy at step 140, and the process is finished for the current prescription. At step 142, if the dosage on the other market prescription is found to be lower than the dosage of the current prescription, the current prescription is categorized as a Titration Increase at step 144, and the process is finished for the current prescription. If the dosage for the other market prescription is not lower than the dosage for the current prescription, i.e., the other market prescription was greater than the current prescription, then the current prescription is categorized as a Titration Decrease at step 146, and the process is finished for the current prescription. If there is another prescription, as determined at step 148, the categorization process continues for that prescription, as indicated by marker A. When the last prescription is reached, the process proceeds to step 160, as described below.

With the process described above, each prescription for a track-able de-identified patient will preferably fall into one category. It is noted that if additional prescription categories are utilized, each prescription may fall into more than one such category. Of course, the sequence of steps described above with respect to steps 120-146 may be changed in order to determine the category of a prescription. Finally, prescription category counts may be added and summarized for each physician or product for any desired time period.

EXAMPLE

Figure 4:
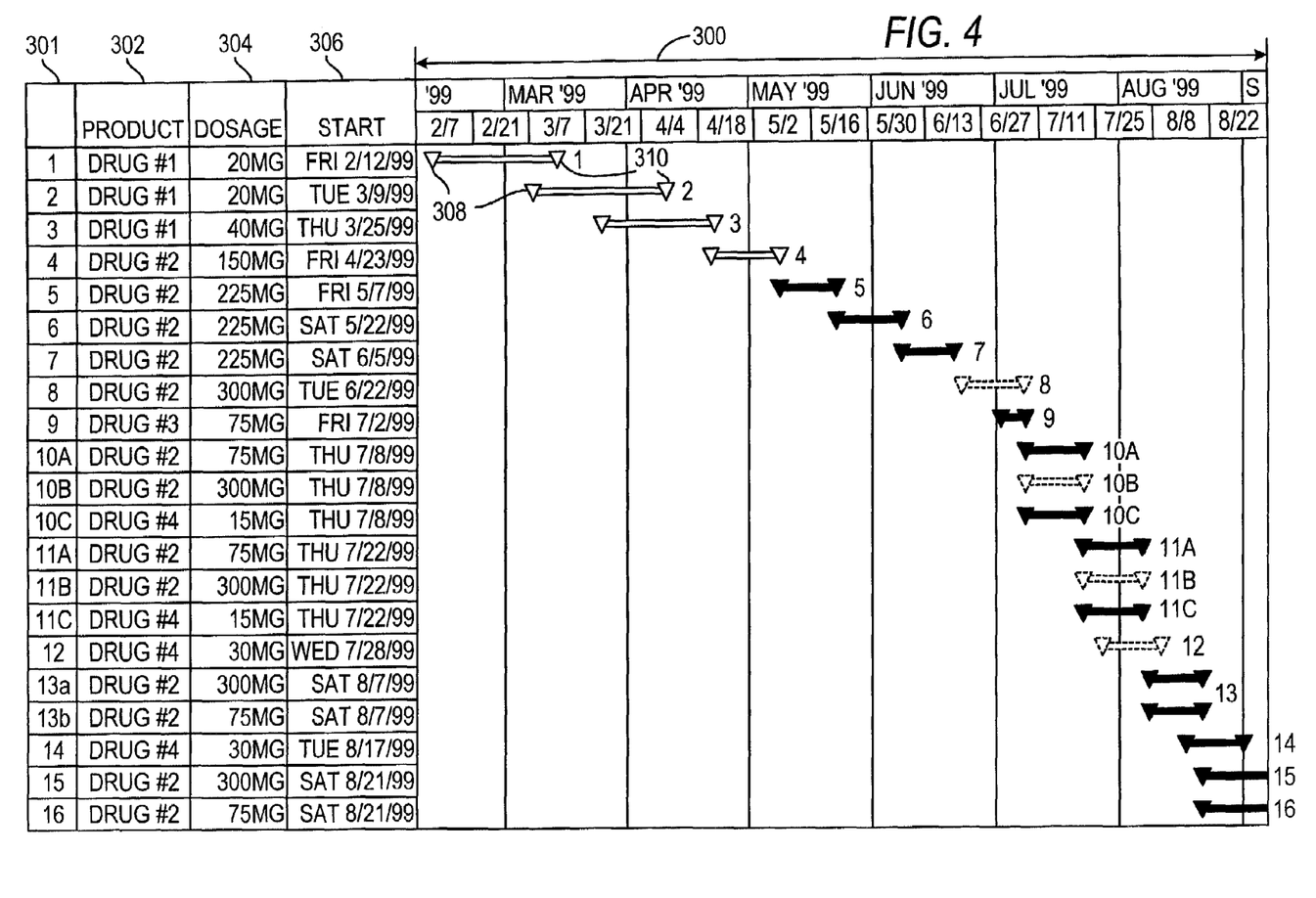
FIG. 4 is an exemplary summary report in accordance with the invention.

FIG. 4 provides an example of prescription categorization. In this example, therapeutic area, or market of interest, is the anti-depressant therapy market. The exemplary time frame 300 includes weekly views from the period beginning with the first quarter of 1999 to the third quarter of 1999. The exemplary observation window consists of the 13 weeks prior to any reporting week. Since these prescriptions all contain the same de-identified patient number, they are categorized according to the rules described above with respect to FIG. 3. The particular prescription number, i.e., Prescription #1 to Prescription #16, appears in column 301. Column 302 indicates the product prescribed, column 304 indicates the dosage, and column 306 has the start date information. Each entry is indicated by a triangle 308 representing the first date of the prescription, and a triangle 310 indicating the last date of the prescription. In this example, Prescription #1 is a New Therapy start. There were no other prescriptions in this market for this de-identified patient number in the prior 13 weeks before Feb. 7, 1999. Based on the process described above, the remaining prescriptions are categorized as shown in TABLE 1

TABLE 1

| Prescription | Category | Comments |
|---|---|---|
| 1 | New Therapy start | No previous market prescription |
| 2 | Continuing Therapy | Same product, same dosage |
| 3 | Titration Increase | 40 mg increased from 20 mg |
| 4 | Therapy Switch | Drug #1 to Drug #2 |
| 5 | Titration Increase | 225 mg increased from 150 mg |
| 6 | Continuing Therapy | Same product, same dosage |
| 7 | Continuing Therapy | Same product, same dosage |
| 8 | Titration Increase | 300 mg increased from 225 mg |
| 9 | Therapy Switch | Drug #2 to Drug #3 |
| 10a | Therapy Switch | Drug #3 to Drug #2 |
| 10b | Add-on Therapy | Drug #2 (75 mg) same day as Prescription 10a |
| 10c | Add-on Therapy | Drug #4 dispensed same day as Prescription 10a |
| 11a | Continuing Therapy | Same product, same dosage as Prescription 10a |
| 11b | Continuing Therapy | Same product, same dosage as Prescription 10b |
| 11c | Continuing Therapy | Same product, same dosage as Prescription 10c |
| 12 | Titration Increase | 30 mg increased from 15 mg |
| 13a | Continuing Therapy | Same product, same dosage as Prescription 11b |
| 13b | Continuing Therapy | Same product, same dosage as Prescription 11a |
| 14 | Continuing Therapy | Same product, same dosage as Prescription 12 |
| 15 | Continuing Therapy | Same product, same dosage as Prescription 13a |
| 16 | Continuing Therapy | Same product, same dosage as Prescription 13b |

Referring again to FIG. 4, the three types of arrows represent the three unique physicians prescribing during this course of treatment, i.e., Physician A in dashed outline, Physician B in solid outline, and Physician C in solid color. At the end of the categorization, the prescriptions may be aggregated to the physician, product, category level for each weekly reporting time period.

Figure 5:
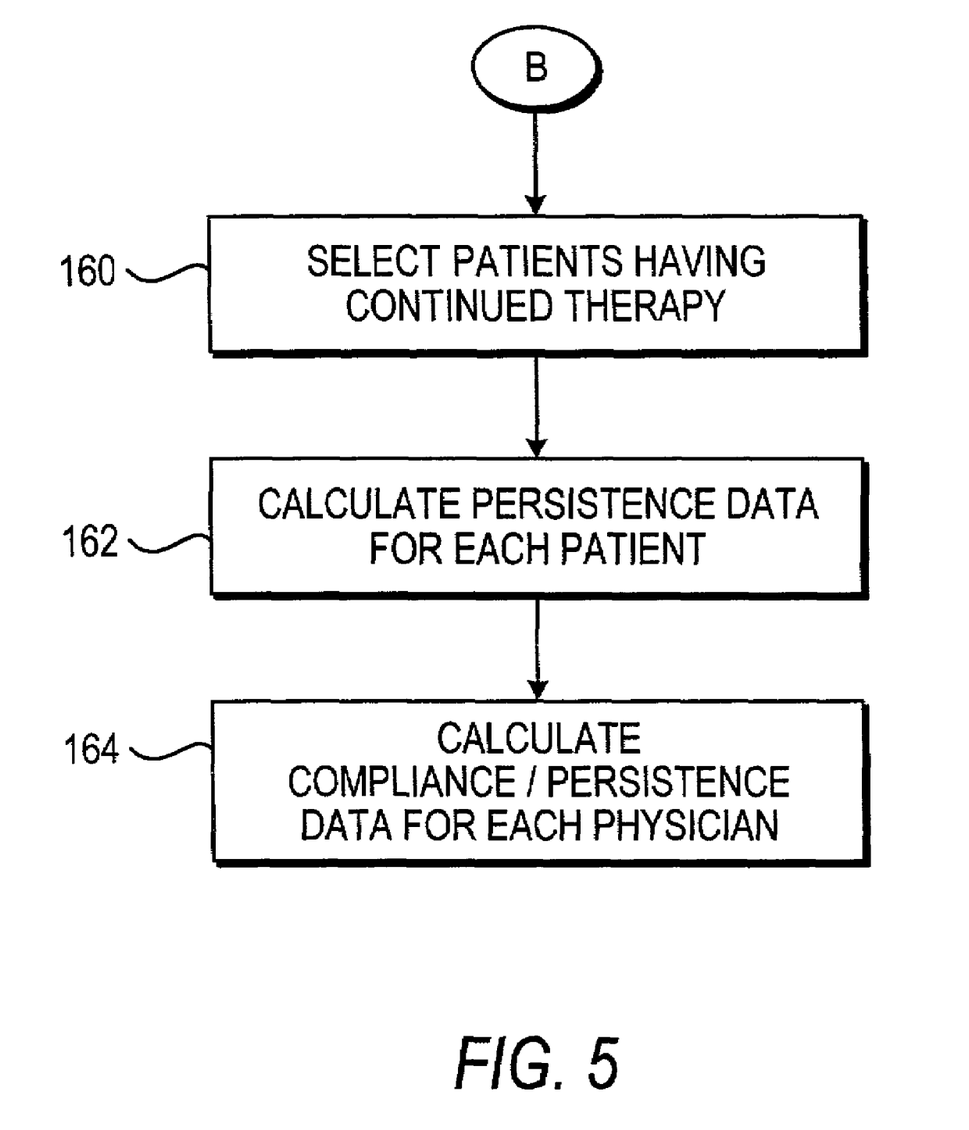
FIG. 5 is flowchart illustrating another portion of the procedure of FIG. 2 in greater detail in accordance with the invention.

FIG. 5 provides further details of step 106 of calculating therapy persistence and compliance. As described above, persistence and compliance are measures of a de-identified patient's diligence in following their doctor's prescription therapy. The time period for evaluation was selected by the user at step 100 (See FIG. 2). In order to perform the persistence evaluation, the analysis according to the invention preferably uses one additional month of data beyond the defined measurement time period at step 160 of FIG. 5, although other time periods could be utilized. For example, to report compliance and persistence for a time period (month or quarter) ending in January, then February data is used. Selecting de-identified patients who continued therapy is determined at step 160. Persistence data is determined for each de-identified patient at step 162. A de-identified patient is labeled "persistent" if they refilled their prescription on time. If they were late in refilling a prescription they are considered "non-persistent." A further stage of the process is to calculate the persistence and compliance data for each physician at step 164. As will be described in greater detail herein, compliance is a physician measure based on the percentage of days that their persistent de-identified patients were supposed to be on a drug therapy divided by the total number of days those de-identified patients were actually on that therapy. These applications are suitable on a weekly, monthly or quarterly basis.

Figure 6:
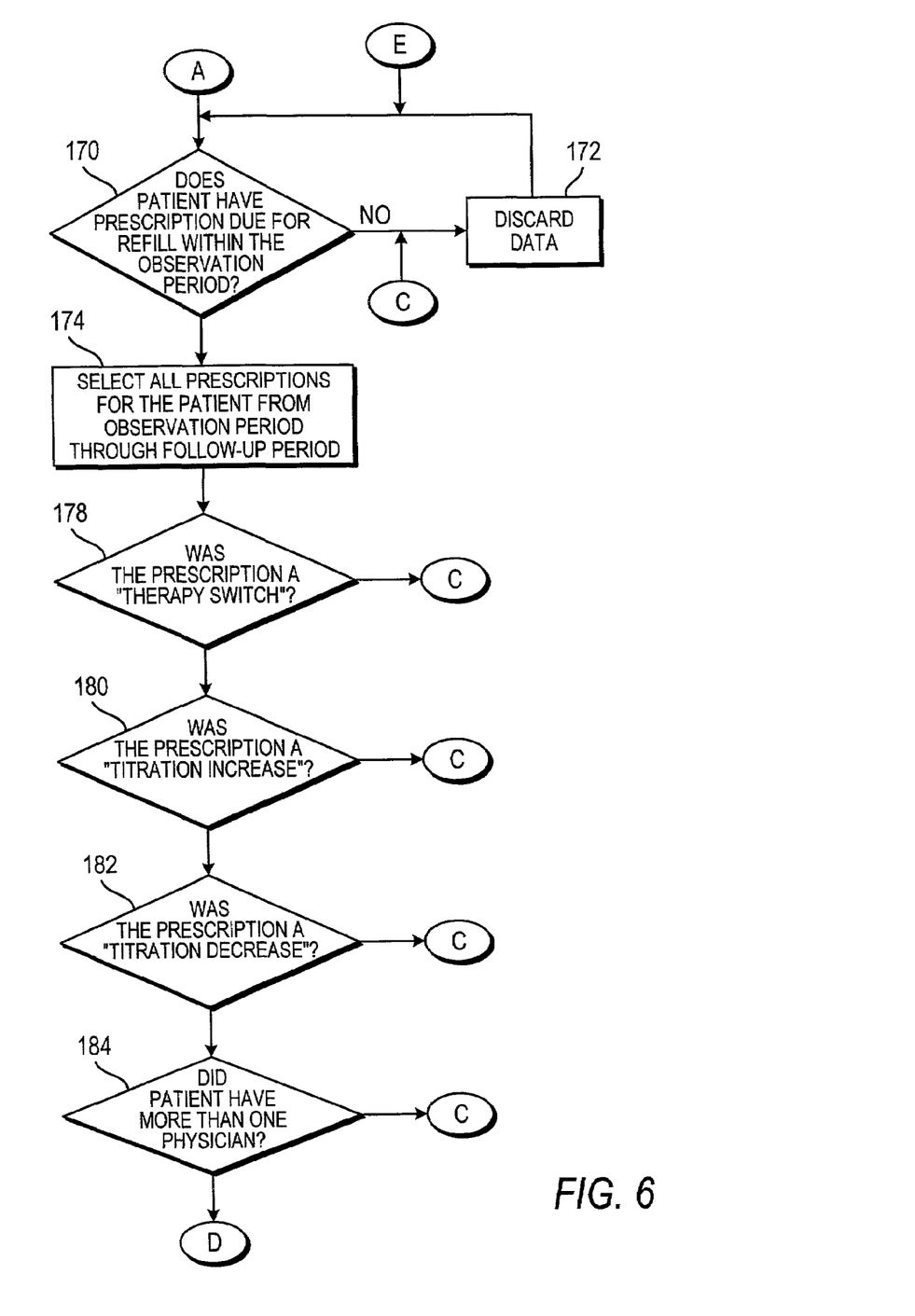
FIG. 6 is a flowchart illustrating a portion of the procedure of FIG. 5 in greater detail in accordance with the invention.

FIG. 6 provides further details with respect to step 160. Step 170 is to determine whether de-identified patients that have at least one market prescription due for refill within the selected time period. If the de-identified patient does not have a prescription due for refill within the selected time period, the data is discarded at step 172, and the next de-identified patient data is evaluated at step 170. In order to calculate the refill due date, the day supply is added to the prescription dispense date on the prescription. Using this due date, step 170 selects all de-identified patients who have a refill due in the observation period. For example, if a January observation period has been chosen, all de-identified patients who have a prescription with a refill due date within the month of January are selected. Patient data is discarded at step 172 for de-identified patients who do not have prescription with a refill due date during the time period.

The next step, step 174, is to select all prescriptions for the de-identified patients remaining from step 170 during of the time period and extending to a follow-up period. For example, for a monthly report, the observation period may be the month of January and the follow-up period is the month of February. Using the prescription categories previously determined in steps 126-146 as described above with respect to FIG. 3, steps 178-184 discard data for any de-identified patient who had either a switch or a titration in therapy. More particularly, at step 178, if the prescription category is determined to be a Therapy Switch, then the data is discarded at step 172 (as illustrated by Marker C). If the prescription is not a Therapy Switch, then the process continues to step 180, in which the data is discarded if the prescription is a Titration Increase. If the prescription is not a Titration Increase, the prescription category is determined at step 182. Here the data is discarded if the prescription is a Titration Decrease. Otherwise, the process determines whether the de-identified patient had more than one physician prescribing prescriptions at step 184. Data is discarded for de-identified patients who had more than one physician at step 172. The remaining data is for de-identified patients having continuing therapy with one doctor, which proceeds to step 190 (FIG. 7).

Figure 7:
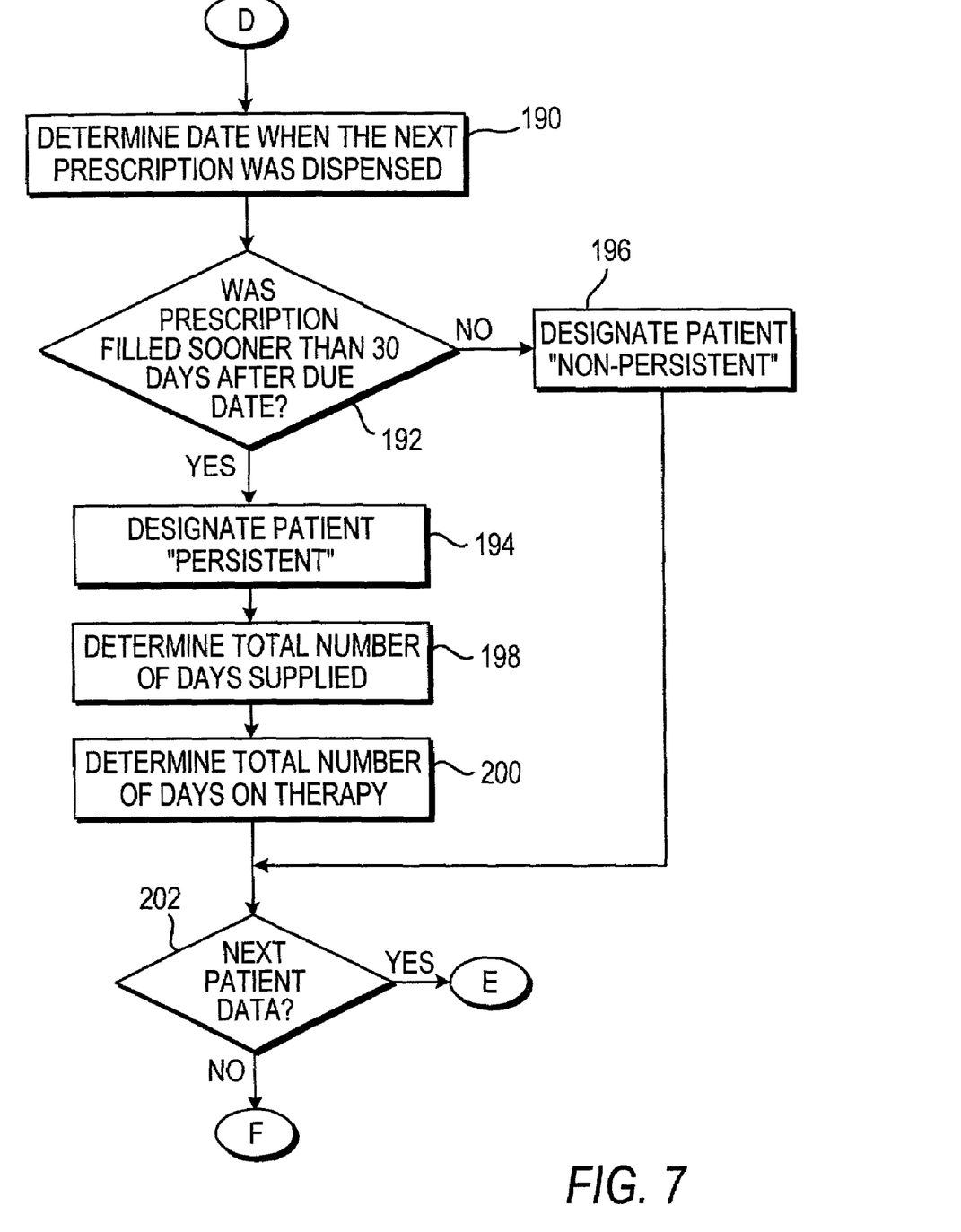
FIG. 7 is a flowchart illustrating another portion of the procedure of FIG. 5 in greater detail in accordance with the invention.

Further details of step 162, i.e., calculating the persistence data for each de-identified patient is illustrated in FIG. 7. A stage in the process is to compare the date of the last prescription within the observation period (e.g., January) and the date of a subsequent prescription for that product in the follow-up period (e.g., February). More particularly, the date of a prescription in the follow-up period is determined at step 190. If it is determined at step 192 that the prescription was filled less than 30 days after the due date, that de-identified patient is labeled "persistent" at step 194.

Otherwise, the de-identified patient is labeled "non-persistent" at step 196. Other time periods could readily be utilized, as could a multi-tiered persistence categorization.

For the persistent de-identified patients, the total number of days supplied for each de-identified patient is determined at step 198. In the embodiment described herein, this data may be obtained from the Retail Pharmacy Prescription data. The total number of days on therapy is determined at step 200. More particularly, the number days on therapy may be calculated by counting the number of days between the dispensed date on the initial prescription in the observation period (e.g., the January prescription) and the dispensed date of the subsequent prescription during the follow-up period (e.g., the February prescription). At step 202, if the next de-identified patient data is to be analyzed, the analysis returns to step 170 for the next de-identified patient, as described with respect to FIG. 6. If there is no additional patient data, the analysis proceeds to step 204 (FIG. 8).

Figure 8:
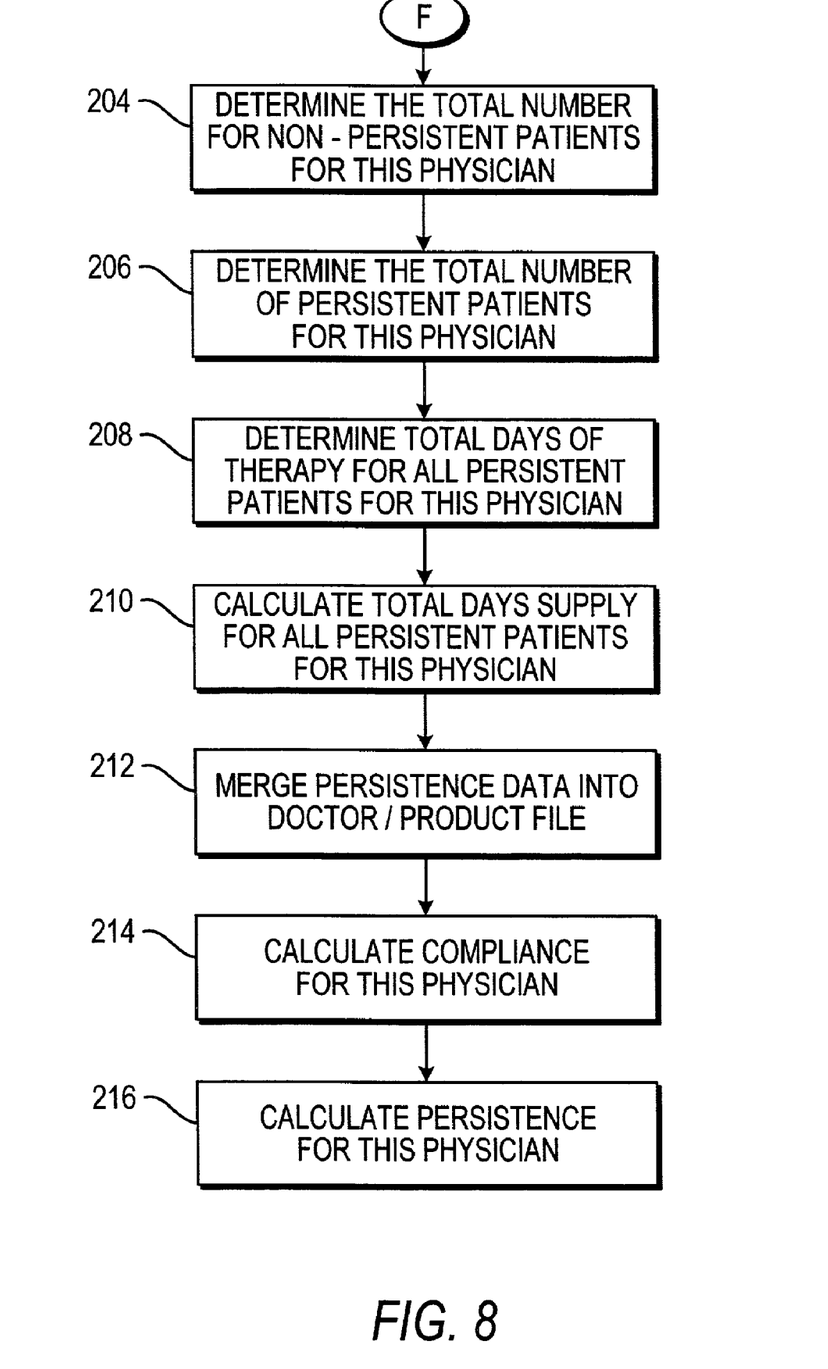
FIG. 8 is a flowchart illustrating a further portion of the procedure of FIG. 5 in greater detail in accordance with the invention

In FIG. 8, further details are described with respect to the calculation of compliance and persistence data for a physician (i.e., step 164 of FIG. 5). At step 204, the total number of non-persistent de-identified patients for a physician is calculated. The total number of persistent de-identified patients is determined at step 206. Next, the total days of therapy for all persistent de-identified patients for this physician are calculated at step 208. The total days supply for all persistent de-identified patients for this physician are calculated at step 210. In the following steps 204, 206, 208, and 210, data for the total number of persistent de-identified patients, the total number of non-persistent de-identified patients, the total number of de-identified patients, i.e., the total number of persistent and non-persistent de-identified patients, the total days supply for persistent de-identified patients, and the total days of therapy for persistent de-identified patients are merged into a single doctor/product level file at step 212.

At step 214, the compliance data for the physician is computed as follows:

$$\text{Compliance} = \text{total days supply}/\text{total days on therapy} \quad (1)$$

Persistence data for the physician/product level is calculated at step 216:

$$\text{Persistence} = \text{Number of persistent patients}/\text{Total number of patients} \quad (2)$$

Figure 2:
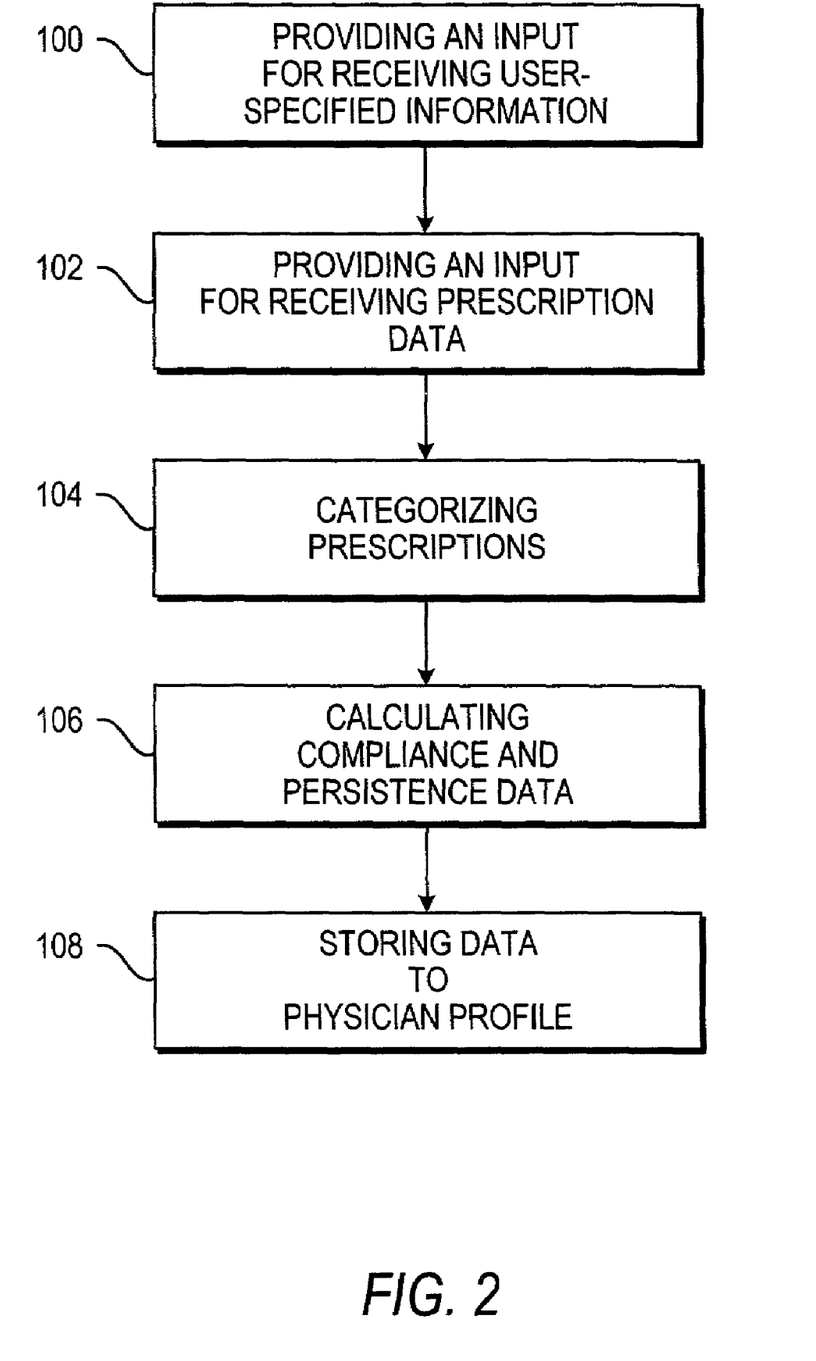
FIG. 2 is a flowchart illustrating an exemplary procedure in accordance with the invention.
Figure 9:
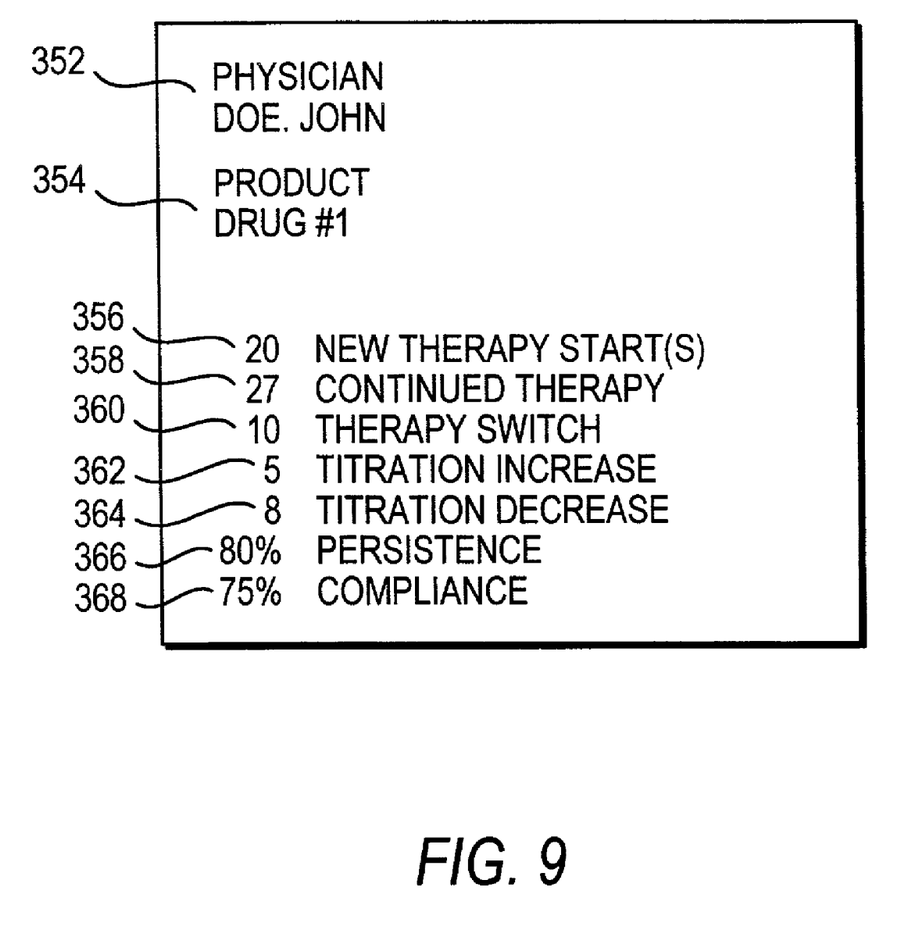
FIG. 9 is a summary of physician prescription information.

As illustrated in FIG. 2, a summary report for each physician is generated at step 108. After the prescriptions are categorized and aggregated to a physician/product/category level, the data is summarized in a report. An example of a summarized record 350 is illustrated in FIG. 9, and stored as output data 26. The level of summarization is to the physician and prescription product. As described above with respect to steps 122-146 of FIG. 3, the categorization of prescriptions occurs at the individual prescription level. Within the time period of interest, the categorized transactions are summed up in each of the categories. In summarized record 350, the data has been summarized for physician 352 and for prescription product 354. The record 350 therefore provides the total number of new therapy starts 356, continued therapy 358, therapy switches 360, titration increases 362 and titration decreases 364 for physician 352 and prescription product 354. The persistence and compliance data calculated in steps 160, 162, and 164 (FIG. 5) are also summarized in report 350. More particularly, summarized record 350 contains data for the persistence 366 and compliance 368 for each physician 352 and prescription product 364. Filters may be applied to enable the system to extract only the information that is actionable by sales representatives. Such filters can be based upon either analytical procedures or business rules or a combination of both. For example, a filter is used to select the top 20 doctors in a territory based on market prescription volume.

In practice, a sales representative may only want to be notified when doctors in his territory start a statistically significant number of patients on a competitor's product for second line therapy. Armed with this knowledge, the sales representative may use a very specific selling message to inform these doctors about the clinical benefits of using the company's brand for second line therapy. Thus, the system described herein could be adapted to extract and deliver exception-based alerts and cycle appropriate information insight to the sales representatives with the right message at the right time.

FIG. 10 illustrates an exemplary report 400 that may be delivered to a sales representative. The territory level report reformat is generated by software code in a back-end reporting system. The system accepts parameters that control what data and how much data are sent to the report. The system customizes the report to the customer's needs based on the parameters selected. Exemplary report 400 has been selected to display statistics for products DRUG #1 and DRUG #2 in the "chronic pain" market of interest 402. Other parameters selected are "sales force" 404 and "territory" 406. A summary portion 410 of the report 400 contains the reported products' shares 414 and market volume 416 by week, which is currently available in today's environment. The report 400 may also provide information about physician practice in a prescriber portion 412. For example, prescriber portion 412 of FIG. 10 illustrates the top four physicians in sections 420a, 420b, 420c, and 420d. In addition, a text message 422a, 422b, 422c, 422d, further describing an observed trend in prescribing practice, is attached to each physician. Statistically significant trends based on the categorized prescription data are determined by applying statistical modeling and trending tests. Each physician is given a score from the statistical trend tests. If the score falls within a user defined range, then that physician is eligible for an alert. For example, Dr. John Doe, once ranked at #21 on market volume, is now ranked at #1 based on longitudinal prescription activity. A sales representative viewing this report now has a clearer picture of Dr. Doe's behavior and can tailor his message appropriately and quickly.

One skilled in the art will appreciate that the present invention can be practiced by other than the described embodiments, which are presented here for purposes of illustration and not of limitation, and the present invention is limited only by the claims that follow.

We claim:

1. A method for generating a profile concerning prescription therapy practices of at least one physician in a therapeutic area of interest, comprising the steps of:
   (a) receiving a plurality of historical de-identified patient prescription records corresponding to prescriptions issued to at least one de-identified patient by at least one physician, each record including de-identified patient identification number, dosage, and prescription product information;
   (b) receiving user-specified information defining a subset of the historical de-identified patient prescription records;
   (c) extracting at least one relevant historical de-identified patient prescription record from the received historical de-identified patient prescription records based on the subset;

(d) for each de-identified patient, comparing dosage and prescription product information contained in a first extracted historical de-identified patient record with dosage and prescription product information contained in a second extracted historical de-identified patient record; and (e) for each comparison made in step (d), categorizing a prescription based on a change in dosage or prescription product.

2. The method of claim 1, wherein the step of receiving user-specified information further comprises receiving information concerning an observation period.

3. The method of claim 1, wherein the step of extracting de-identified patient prescription records further comprises discarding a historical de-identified patient prescription record having an eligibility of shorter duration than the observation period.

4. The method of claim 1, wherein the step of categorizing prescriptions further comprises categorizing a prescription of a product as a new therapy start when a de-identified patient has had no other prescriptions in a therapeutic area to which the product pertains.

5. The method of claim 1, wherein the step of categorizing prescriptions further comprises categorizing a prescription as a therapy switch when a de-identified patient has had no other prescriptions of the product, and when the de-identified patient has had a prescription of a second product within a therapeutic area to which the product pertains that was not prescribed on the same day as the prescription.

6. The method of claim 1, wherein step of categorizing prescriptions further comprises categorizing a prescription as an add-on therapy when the de-identified patient had no other prescriptions for the product but had a prescription for a second product within the therapeutic area to which the product pertains that was prescribed on the same day.

7. The method of claim 1, wherein the step of categorizing prescriptions further comprises categorizing a prescription as a titration decrease when a de-identified patient has previously had a prescription for the product at a higher dosage.

8. The method of claim 1, wherein the step of categorizing prescriptions further comprises categorizing a prescription as a titration increase when a de-identified patient has previously had a prescription for the product at a lower dosage.

9. The method of claim 1, wherein the step of categorizing prescriptions further comprises categorizing a prescription as continued therapy when a de-identified patient has previously had a prescription for the product at the same dosage.

10. A method for generating a profile concerning prescription therapy practices of at least one physician in a therapeutic area of interest comprising the steps of:

(a) receiving a plurality of historical de-identified patient prescription records corresponding to prescriptions issued to at least one de-identified patient by at least one physician, each record including de-identified patient identification number, prescription product information, date dispensed, dosage, number of days supplied, and refill information;

(b) receiving user-specified information defining a subset of the historical de-identified patient prescription records;

(c) extracting at least one relevant historical de-identified patient prescription record from the received historical de-identified patient prescription records based on the subset;

(d) for each de-identified patient, comparing dosage and prescription product information contained in a first extracted historical de-identified patient record with dosage and prescription product information contained in a second extracted historical de-identified patient record;

(e) for each comparison made in step (d), categorizing a prescription based on a change in dosage or prescription product;

(f) extracting at least one relevant historical de-identified patient prescription record from the prescriptions categorized at step (e) based on the refill information;

(g) for each de-identified patient, determining a refill due date based on the dosage and the number of days supplied for a first prescription;

(h) for each de-identified patient, comparing the refill due date of the first prescription with the date dispensed for a second prescription; and (i) for each comparison made in step (h), categorizing the de-identified patient based on the duration between the refill due date of the first prescription and the date dispensed for the second prescription.

11. The method of claim 10, wherein the step of receiving user-specified information further comprises receiving information concerning an observation period.

12. The method of claim 11, further comprising a step of discarding, after step (e), a historical de-identified patient prescription record for a de-identified patient having more than one physician during the observation period.

13. The method of claim 11, wherein the step of extracting de-identified patient prescription records based on refill information further comprises discarding a historical de-identified patient prescription record not having a refill due within the observation period.

14. The method of claim 10, wherein the step of categorizing prescriptions further comprises categorizing a prescription of a product as a new therapy start when a de-identified patient has had no other prescriptions in a therapeutic area to which the product pertains.

15. The method of claim 10, wherein the step of categorizing prescriptions further comprises categorizing a prescription as a therapy switch when a de-identified patient has had no other prescriptions of the product, and when the de-identified patient has had a prescription of a second product within a therapeutic area to which the product pertains that was not prescribed on the same day as the prescription.

16. The method of claim 15, further comprising a step of discarding, after step (e), a historical de-identified patient prescription record for a prescription categorized as a therapy switch.

17. The method of claim 10, wherein the step of categorizing prescriptions further comprises categorizing a prescription as a titration decrease when a de-identified patient has previously had a prescription for the product at a higher dosage.

18. The method of claim 17, further comprising a step of discarding, after step (e), a historical de-identified patient prescription record for a prescription categorized as a titration decrease.

19. The method of claim 10, wherein the step of categorizing prescriptions further comprises categorizing a prescription as a titration increase when a de-identified patient has previously had a prescription for the product at a lower dosage.

20. The method of claim 19, further comprising a step of discarding, after step (e), a historical de-identified patient prescription record for a prescription categorized as a titration increase.

21. The method of claim 10, wherein the step of categorizing the de-identified patient based on the duration between the due date of the first prescription and the fill date of the second prescription further comprises categorizing the de-identified patient as persistent if the duration is shorter than a predetermined number of days.

22. The method of claim 21, wherein the step of categorizing the de-identified patient based on the duration between the due date of the first prescription and the fill date of the second prescription further comprises categorizing the de-identified patient as non-persistent if the duration is greater than a predetermined number of days.

23. The method of claim 22, further comprising a step of determining, after step (i), the total number of persistent de-identified patients and the total number of non-persistent de-identified patients for each physician.

24. The method of claim 23, further comprising a step of calculating, after the step of determining the total number of persistent de-identified patients and the total number of non-persistent de-identified patients for each physician, persistence of the physician by dividing the total number of persistent de-identified patients by the total number of de-identified patients for each physician.

25. A system for generating a profile concerning prescription therapy practices of at least one physician in a therapeutic area of interest, comprising:
(a) a mass storage device for storing a plurality of historical de-identified patient prescription records corresponding to prescriptions issued to at least one de-identified patient by at least one physician, each record including a de-identified patient identification number, dosage, number of days supplied and prescription product information, dosage, fill date, and number of days supplied;
(b) an input device, coupled to the mass storage device, for receiving user-specified information which defines a subset of the plurality of historical de-identified patient prescription records;
(c) a prescription categorizer, coupled to the input device, configured to compare the dosage and the prescription product information contained in a first historical de-identified patient prescription record with the dosage and prescription product information contained in a second historical de-identified patient prescription record, and to categorize a prescription based on a change in dosage or prescription product; and
(d) a persistence calculator, coupled to the prescription categorizer, configured to determine the due date of a first prescription based on the dosage and the number of days supplied, to compare the due date of the first prescription with the fill date of a second prescription, and to categorize the de-identified patient based on the duration between the due date of the first prescription and the fill date of the second prescription.

26. The system of claim 25, wherein the prescription categorizing is configured to categorize a prescription of a product as a new therapy start when a de-identified patient has had no other prescriptions in a therapeutic area to which the product pertains.

27. The system of claim 25, wherein the prescription categorizing is configured to categorize a prescription of a product as a therapy switch when a de-identified patient has had no other prescriptions of the product, and when the de-identified patient has had a prescription of a second product within a therapeutic area to which the product pertains that was not prescribed on the same day as the prescription.

28. The system of claim 25, wherein the prescription categorizing is configured to categorize a prescription of a product as an add-on therapy when the de-identified patient had no other prescriptions for the product but had a prescription for a second product within the therapeutic area to which the product pertains that was prescribed on the same day.

29. The system of claim 25, wherein the prescription categorizing is configured to categorize a prescription of a product as a titration decrease when a de-identified patient has previously had a prescription for the product at a higher dosage.

30. The system of claim 25, wherein the prescription categorizing is configured to categorize a prescription of a product as a titration increase when a de-identified patient has previously had a prescription for the product at a lower dosage.

31. The system of claim 25, wherein the prescription categorizing is configured to categorize a prescription of a product as continued therapy when a de-identified patient has previously had a prescription for the product at the same dosage.

32. The system of claim 25, wherein the persistence calculator is further configured to categorize the de-identified patient as persistent if the duration between the due date of the first prescription and the fill date of the second prescription is shorter than a predetermined number of days.

33. The system of claim 25, wherein the persistence calculator is further configured to categorize the de-identified patient as non-persistent if the duration between the due date of the first prescription and the fill date of the second prescription is greater than a predetermined number of days.

34. The system of claim 25, wherein the persistence calculator is further configured to determine the total number of persistent de-identified patients and the total number of non-persistent de-identified patients for each physician.

35. The system of claim 34, wherein the persistence calculator is further configured to determine the persistence of the physician by dividing the total number of persistent de-identified patients by the total number of de-identified patients for each physician.

* * * * *